United States Patent [19]

Brandely et al.

[11] Patent Number: 5,582,822
[45] Date of Patent: Dec. 10, 1996

[54] TREATMENT OF LEUKEMIA USING INTERLEUKIN 2

[75] Inventors: Maud Brandely, Paris; Dominique Maraninchi, Marseille, both of France

[73] Assignee: Roussel Uclaf, France

[21] Appl. No.: 315,890

[22] Filed: Sep. 30, 1994

Related U.S. Application Data

[63] Continuation of Ser. No. 951,202, Sep. 25, 1992, abandoned, which is a continuation of Ser. No. 598,555, Oct. 16, 1990, abandoned.

[30] Foreign Application Priority Data

Oct. 17, 1989 [FR] France ................. 89-135461

[51] Int. Cl.⁶ .................................... A61K 38/20
[52] U.S. Cl. ................. 424/85.2; 530/351; 514/2

[58] Field of Search .......... 530/351; 424/85.1, 424/85.2; 514/2, 21

[56] References Cited

PUBLICATIONS

Gottlieb et al., Br. J. Cancer, vol. 60, pp. 610–615, 1989.
Chiao et al., Proc. Natl. Acad. Sci., vol. 83, pp. 3432–3436 1986.

*Primary Examiner*—John Ulm
*Assistant Examiner*—Sally P. Teng
*Attorney, Agent, or Firm*—Bierman and Muserlian

[57] ABSTRACT

A method of treating leukemia in warm-blooded animals suffering from leukemia comprising administering to said warm-blooded animals an amount of polypeptide having human interleukin 2 activity sufficient to treat leukemia.

7 Claims, 3 Drawing Sheets

TREATMENT OF LEUKEMIA USING INTERLEUKIN 2

This application is a continuation of U.S. patent application Ser. No. 951,202 filed Sep. 25, 1992 which is a continuation of U.S. patent application Ser. No. 598,555 filed Oct. 16, 1990, both now abandoned.

Interleukin 2 (IL2) which is a lymphokine produced by activated T lymphocytes possesses an immunomdulating activity and an anti-tumor activity described, for example, by Fletcher et al (Lymphokine Research, Vol. 6, (1987), p. 47–57, activities which include in particular the capacity to initiate the proliferation of T lymphocytes and the induction of cytotoxicity of NK (natural killer) cells and LAK (lymphokine activated killer) cells, It has been observed that the administration of IL2, either alone at high dosage, or combined with LAK cells, is able to induce the regression of certain established cancers in mice and in patients having metasiatic cancers such as melanoma, cancer of the kidney, colorectal cancer or non-Hodgkinsonian lymphoma (Rosenberg, et al, N. Engl. J. Med. (1987), Vol. 516, p. 889–897.

No clinical result has shown the effectiveness of the therapy with IL2 alone or combined with an adoptive immunotherapy in the various known chronic or acute leukemias, notably in acute myeloid leukemia (AML). The phenomena of disregulation leading to the proliferation of leukemia cells are complex and it is generally admitted that their control necessitates the combined use of different factors of differentiation, notably the use of IL2 with, for example an interferon, the factor of tumerous necrosis, another interleukin or other differentiation factors, as described, for example, for the chronic lymphoid leukemia in patent application WO 88/06991.

It has been suggested and confirmed that IL2 stimulates in vitro in a significant way the proliferation of blast cells of patients suffering from AML (Carron et al, Br. J. Haematol; Vol. 71 (1), (1989), p. 168.).

OBJECTS OF THE INVENTION

It is an object of the invention to provide a novel method of treating leukemias with a polypeptide having human interleukin activity.

This and other objects and advantages of the invention will become obvious from the following detailed description.

THE INVENTION

The novel method of the invention of treating leukemia in warm-blooded animals suffering from leukemia comprises administering to said warm-blooded animals an amount of polypeptide having human interleukin 2 activity sufficient to treat leukemia. A polypeptide having the activity of human interleukin 2 means a polypeptide having the human IL2 activity, natural human IL2, recombinant human IL2 which is obtained by recombinant DNA technology, for example, such as that described by Taniguchi et al, [Nature, (1983), Vol. 302, p. 305–310)] or in Patent EP 91S30 B, alleles or derivatives of these products as described for example by Ju et al [J. Biol. Chem., (1987), Vol. 262, p. 5723≧5731)].

The leukemias of the invention include chronic myeloid or lymphoid leukemias and acute lymphoid or non-lymphoblast leukemias such as the myeloid leukemias in a general fashion characterized by the proliferation of blast cells.

A preferred method of the invention treats as the leukemia an acute myeloid leukemia as diagnosed by the usual histological, cytological and biological examinations. The method of the invention is intended for the treatment of AML, for the treatment of a relapse of this or for the preventative treatment of relapse. The use of IL2 in a treatment shows an effectiveness shown by a response rate of about 20% in patients suffering from AML either resistant to conventional chemotherapy, or in relapse after chemotherapy or after a bone marrow transplant.

Preferably, the human IL2 is a pure recombinant $IL_2$ or alleles or derivatives of this such as described above, for which known purification techniques are used which allow the preparation of pure products. Also useful as the IL2 is a non-glycosylated recombinant IL2 in reduced form. The non-glycosylated IL2 used is that having the natural IL2 sequence with 133 amino acids and optionally a supplementary N-terminal methionine, of which the 3 cysteines in position 58, 105 and 125 are in reduced form manifesting a biological activity comparable to that of oxidized IL2 having the same sequence comprising a disulfide bridge in position 58–105.

An example of the preparation of reduced IL2 starting with a strain of *E. Coli* is given further on in the experimental part. Reduced form means that the cysteine remainders which IL2 contains, contain a free sulfhydryl group of which the determination is done, for example, by spectrophotometry with dithiodipyridine as reagent of the thiois. The biological activity is determined by measurement of the proliferation of the leukemic cell lines of mice dependent on IL2, CTLL-2, with a colormetric test with a tetrazolium salt [Mossmann, Immunol. Meth (1983), Vol. 65, p. 5–63]. The specific activity of recombinant IL2 used is at least equal to $0.5 \times 10^6$ U BRMP/mg, preferably $1 \times 10^7$ U BRMP/mg. The unit of IL2 activity is defined as the quantity which produces 50% of the maximum response in the test. A "Biological Response Modifier Program (BRMP) reference agent Human IL2 (jurkat)" sample supplied by the National Cancer Institute (NCI) is used as a standard.

Preferably, the IL2 is administered at a dose of 2 to $20 \times 10^6$ U/M$^2$ per injection. The composition of the invention may be administered for example, intravenously by slow bolus or by continuous perfusion, by muscular route or subcutaneously.

Preferably, the IL2 is administered intravenously by slow bolus at a dose of about $8 \times 10^6$ U/M$^2$ per injection and the IL2 administered in a repeated fashion at least twice a day in a cycle of several days per week and preferably in a repeated fashion for at least 3 nonconsecutive weeks.

The administered dose, the frequency of injection and the duration of treatment varies according to the condition of the patient. The daily dose is generally between $2 \times 10^6$ U/M$^2$ per 24 hours and $30 \times 10^6$ U/M$^2$ per 24 hours, preferably of the order of $30 \times 10^6$ U/M$^2$/24 hours in a cycle of several days for an adult or infant.

The IL2 is contained in a pharmaceutical composition preferably lyophilized in a dispensing bottle containing 0.1 to 2 mg of active ingredient and which is reconstituted with distilled water for injection. The solution is immediately diluted with a solute, for example. 0.9% sodium chloride or 5% glucose for the administration of a slow bolus. Slow bolus means a perfusion of short duration, for example, 15 minutes.

In a preferred method of the invention, the IL2 is reduced recombinant IL2 and the dose is $8 \times 10^6$ U/M$^2$ per injection. The frequency of injection is every 8 hours (3 doses/day) or every 12 hours (2 doses/day) in a cycle of 5 consecutive days. The duration of the administration is 3 non-consecutive weeks, representing about $360 \times 10^6$ U/M$^2$ and 36 mg administered in total for an adult intravenously by slow bolus of 15 minutes.

REFERRING NOW TO THE FIGURES

Preparation of reduced recombinant human IL2 (r-hIL2):

The IL2 is prepared starting with granules which are obtained by centrifuging cultures of an *E. coli* strain converted using a plasmid containing the coding sequence for native IL2 and capable of accumulating IL2 in that form inside cells as described by Sato et al [J. biochem. (1987), Vol. 101, p. 525–534]. The cells thus obtained from a 10 liter fermentor are subjected to a breaking up in a Manton Gaulin homogenizer.

Figure 1A:
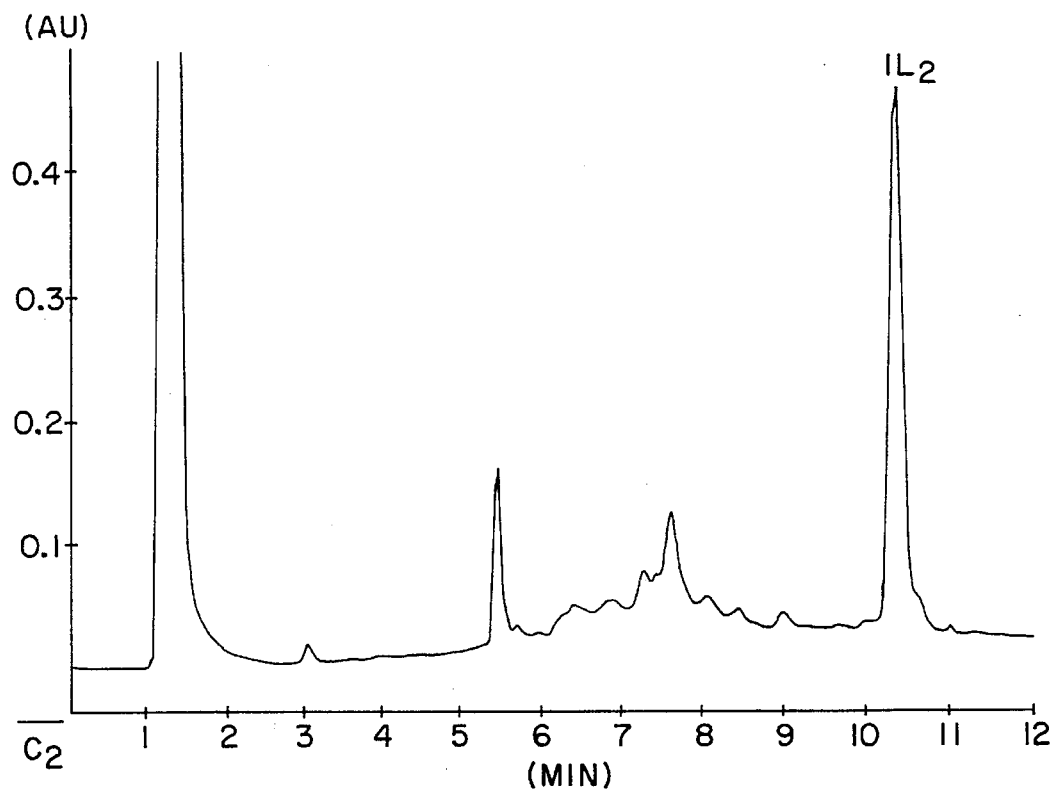
FIG. 1a is an analytical RP-HPLC chromatogram of the crude extract of 8M guanidine of the preparation and FIG. 1b is an analytical RP-HPLC chromatogram of the reduced and oxidized IL$_2$ standard.
Figure 1B:
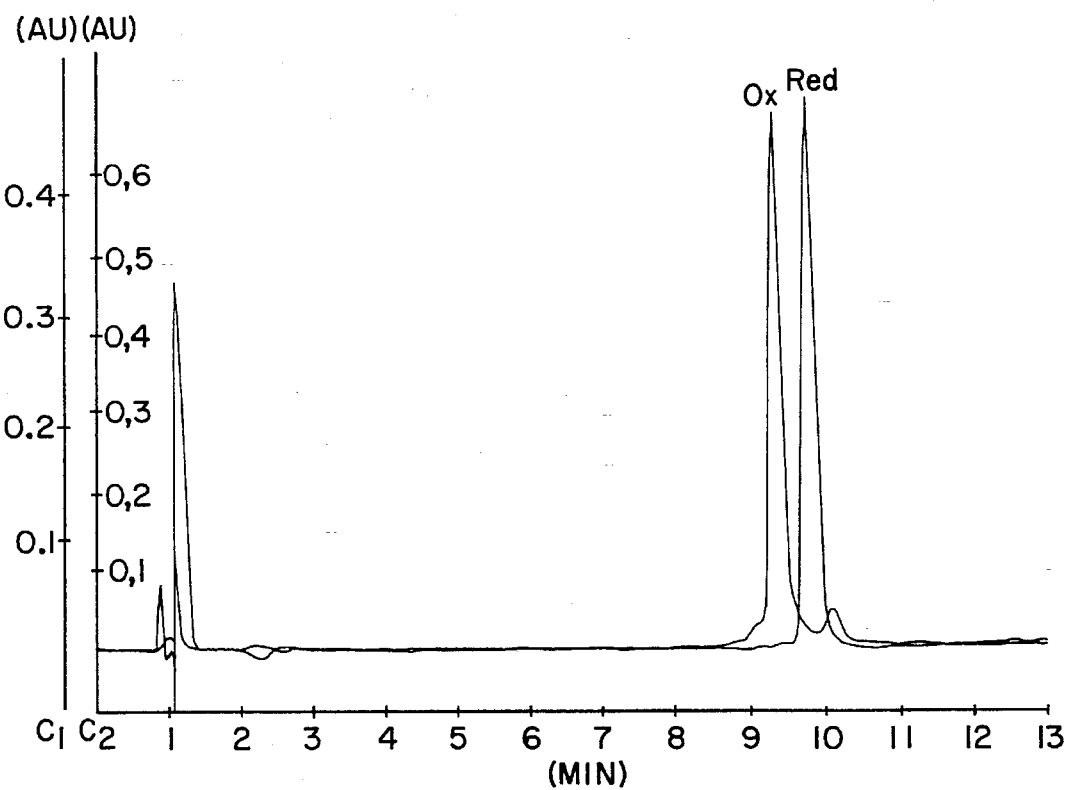
Figure 2:
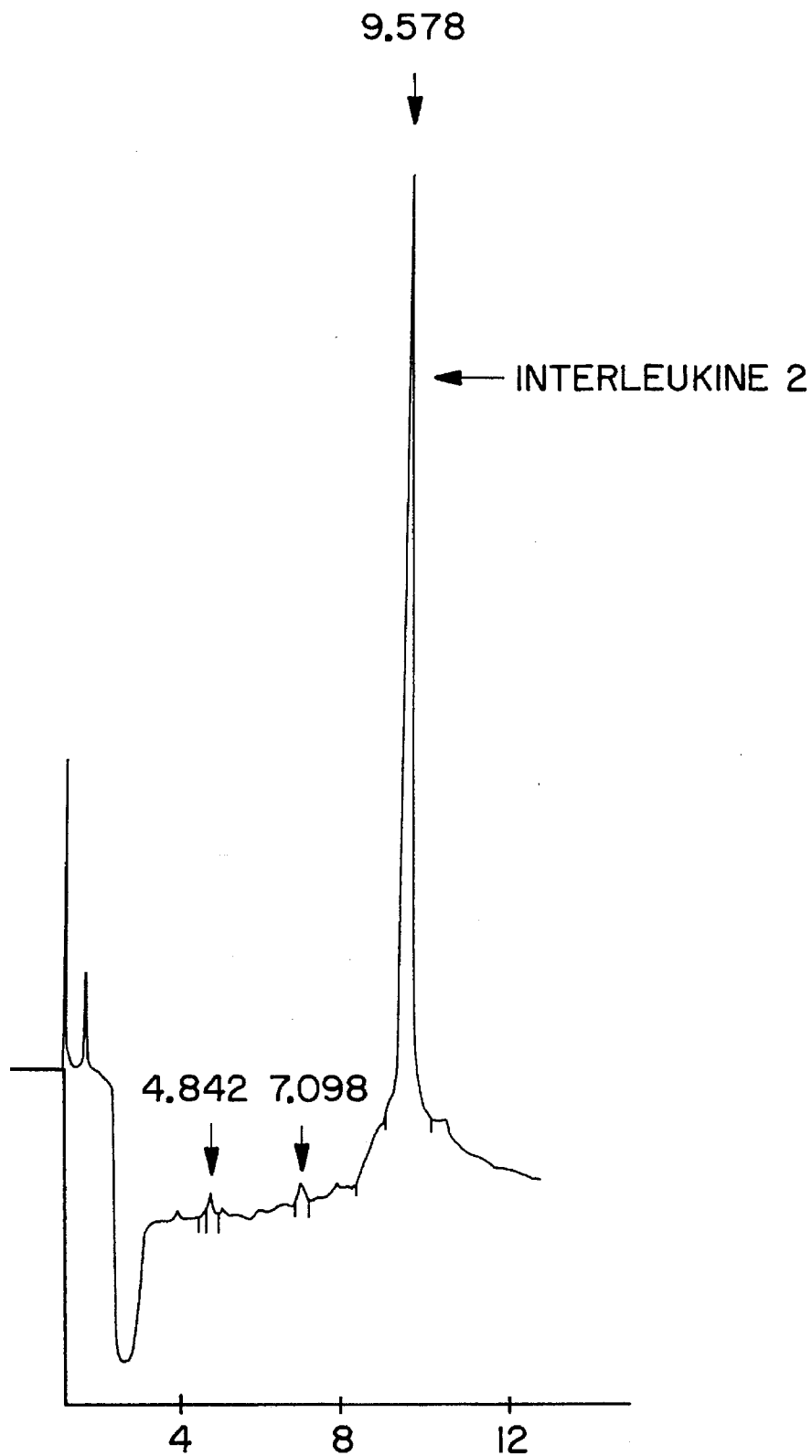
FIG. 2 is an analytical RP-HPLC chromatogram of the "resolubilization" of the preparation and FIG. 3 is an RP-HPLC chromatogram of the "principal fraction" of the preparation.

Starting with the isolated and washed cellular debris (90–170 g by damp weight), the IL2 is solubilized in 2.5 volumes of Tris, HCl 20 mM pH 8 buffer containing 8M guanidine hydrochloride (Gu, HCl) and Dithiothreitol (DTT) 100 mM. The amount of IL2 solubilized (1.5 to 2.5 g) is estimated by analytic RP-HPLC on a C4 VYDAC (0.46×15 cm) column 300 A, 5 microns, at a rate of 2 cm$^3$/mn, with a linear gradient of acetonitrile (30 to 70% over 10 minutes) containing 0.1% of TFA. A spectrophotometric detection at 280 nm is evaluated after calibration with an IL2 standard (FIG. 1a and FIG. 1b). The IL2 is then precipitated by lowering the concentration of Gu, HCl to 2M, in the presence of DTT. After washing the precipitate with an aqueous solution of 0.1% TFA until a pH of the supernatant of less than 5.0 has been obtained, the IL2 is solubilized in an aqueous solution of 20% acetonitrile and 0.1% TFA The "resolubilization" obtained, which contains according to analytic RP-HPLC (FIG. 2) a reduced IL$_2$ content of greater than 85% has a biological activity of less than $0.01 \times 10^7$ U/mg of reduced IL2 and a content of sulfhydryl groups of 2.85 SH/mole of reduced IL2. A fraction of the solution obtained, corresponding to about 200 mg of IL2 estimated by analytical RP-HPLC, was diluted to adjust the concentration of acetonitrile to less than 10% 0.1% TFA, % then applied to a C4 VYDAC (5.7×30 cm) column. The IL2 was eluted at a rate of 100 ml/mn using a linear gradient of aceonitrile (30 to 80% over 40 minutes) containing 0.1% TFA, at a concentration of about 60% of acetonitrile in a major peak detected by spectrophotometry at 280 nm and analyzed by RP-HPLC.

Figure 3:
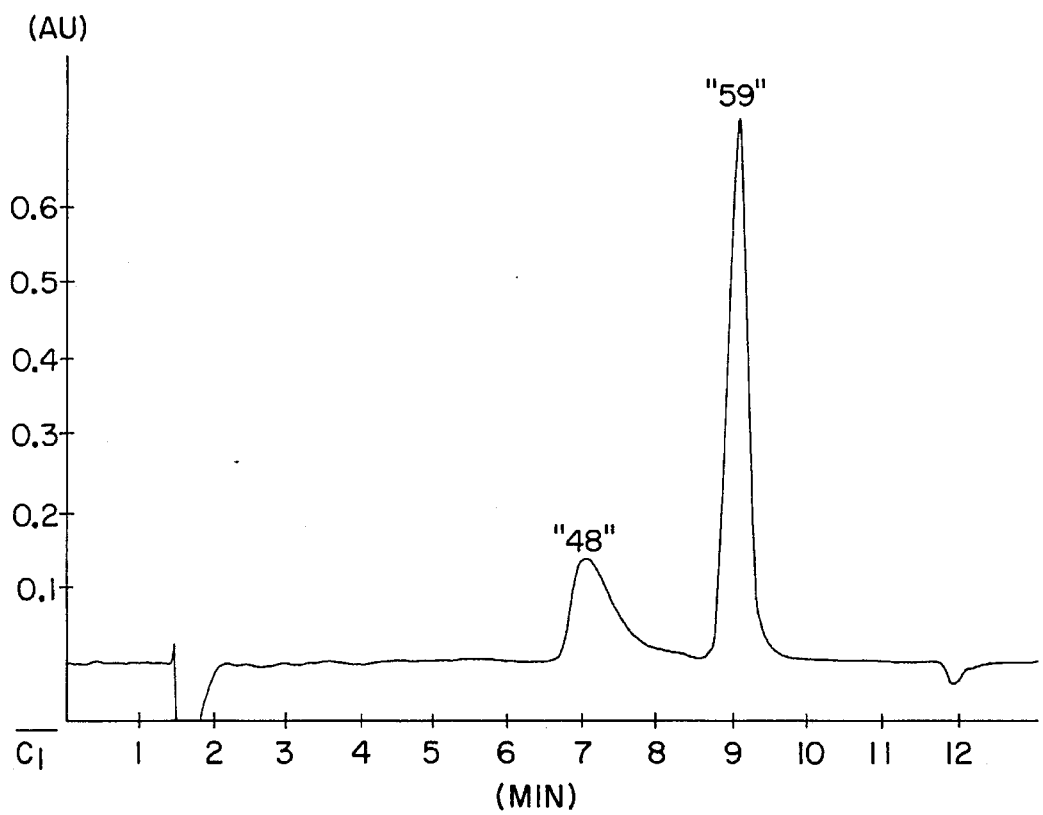

The "principal fraction" collected which contains the reduced IL2 was immediately diluted with 2 volumes of an aqueous solution of 5% citric acid and applied to a C4 VYDAC 5.7×30 cm) column which was developed with a linear gradient of isopropanol (20 to 70% over 40 minutes) containing 0.5% citric acid at a rate of 50 ml/mn. The effluent, followed by spectrophotometry at 280 nm shows the successive elution of a minor peak at a concentration of about 48% of isopropanol (fraction "48") and a major peak at a concentration of about 59% of isopropanol fraction "59") (FIG. 3). The "59" fraction was collected and it was stable, preserved at 0° C. for at least 24 hours away from air.

Figure 4:
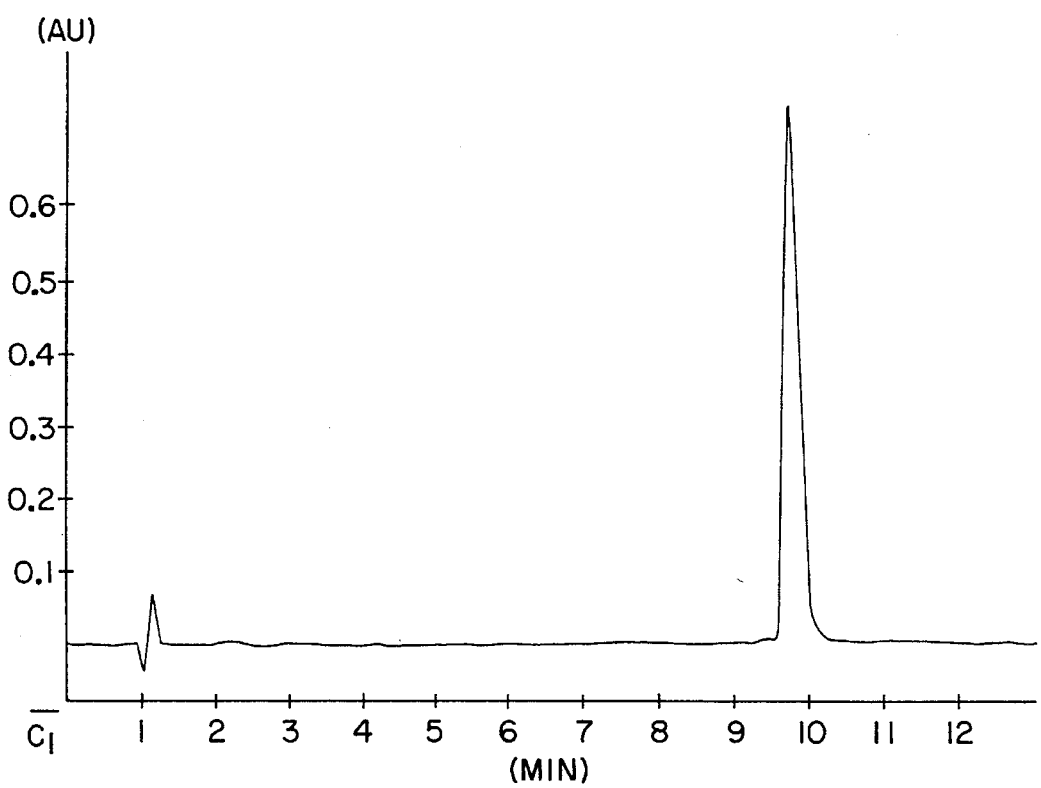
FIG. 4 is an analytical RP-HPLC chromatogram of fraction "59" of the preparation.

After elimination of the isopropanol by azeotropic distillation under vacuum, the "59" fraction was analyzed by analytical RP-HPLC and gave a homogeneous peak (FIG. 4) eluted at about 60% acetonitrile whereas the reference oxidized IL2 was eluted at about 57% acetonitrile (FIG. 1b). The "59" fraction which, after elimination of isopropanol, had a concentration of IL2 greater than 1 mg/ml and a pH of 3+0.5 could be preserved at +4° C. away from air for at least a week or could be immediately lyophilized or formulated to obtain a pharmaceutical composition. The lyophilized "59" fraction was determined for biological activity by the in vitro test for proliferation of CTLL-2 cells, and had a specific activity of $1.3 \pm 0.5 \times 10^7$ U/mg coinparable to that of the native IL2.

The free sulfhydryl group content of the lyophilized "59" fraction determined by the colorimetrical method wtih dithiopyridine was 2.94 SH/mole compared with 0.76 SH/mole for the reference oxidized IL2. 150 to 300 mg titrated by analytic RP-HPLC of reduced r-hIL2 containing 3 SH groups by biologically active, homogeneous in RP-HPLC were obtained in the "59" fraction starting with a 10 liter fermentor.

In the following examples, there are described several preferred embodiments to illustrate the invention. However, it should be understood that the invention is not intended to be limited to the specific emobodiments.

Example 1: Pharmaceutical composition for perfusion.

A preparation for injection by intravenous perfusion of the following formula was prepared

| | |
|---|---|
| reduced IL2 | 0.5 mg |
| citric acid | 5 mg |
| mannitol | 50 mg |
| sterilized water | 1 ml |
| 5% glucose | 50 ml |

Example 2: Clinical study in the treatment of AML.

The study included patients having a primary AML of histological diagnosis (M1 to M5 type according to the FAB classification) for which there had been an induction chemotherapy followed by either a maintenance chemotherapy, or an autologous bone marrow transplant (called ABMT) and of which a prior diagnosis had been established the relapse or the resistant character to chemotherapy, evaluated by the presence of more than 10% of blasts in two samples of bone marrow carried out in at least one week intervals, for example, at two week intervals.

The compositions of IL2 prepared by the invention were injected at doses of $8 \times 10^6$ U/M$^2$ being 0.8 mg/H$^2$ per injection, at the rate of an injection every 8 hours for 5 consecutive days during the first week, then the same dose as above at the rate of an injection every 12 hours for 5 consecutive days during the third week and the fifth week, by intravenous route with slow bolus of 15 minutes. The compositions described in Example 1 were used. The evaluation of the patients was done before and after treatment with IL2 on samples of bone marrow by determination of the percentage of blasts and evaluation of the state of differentiation of medullary precursors. On 11 re-evaluated patients, the following responses were obtained:

| Patient | Age | Sex | Type | Haematological state at inclusion | % of Medullary blasts after IL2 | | | | Response |
|---|---|---|---|---|---|---|---|---|---|
| | | | | | D0 | D8 | D14 | D36 | |
| 1 | 68 | M | M5 | 1st relapse under chemo. | 30 | 4 | 2 | 0 | CR |
| 2 | 17 | F | M5 | Primary resistance | 35 | 83 | 80 | 80 | Failure |
| 3 | 60 | M | M5 | 2nd relapse resistant to chemo | 42 | 24 | 43 | 16 | Failure |
| 4 | 5 | M | M5 | 3rd relapse after ABMT | 81 | 3 | ND | 0 | CR |
| 5 | 56 | M | M4 | 1st relapse under chemo | 13 | ND | 19 | 60 | Failure |
| 6 | 25 | M | M2 | 1st relapse under chemo | 14 | ND | ND | 0 | Failure |
| 7 | 45 | M | M4 | Primary resistance | 75 | ND | 22 | 33 | Failure |
| 8 | 28 | M | M4 | 1st relapse after ABMT | 61 | 89 | 57 | 70 | Failure |
| 9 | 53 | F | M1 | 1st relapse resistant to chemo | 83 | 74 | 93 | 92 | Failure |
| 10 | 59 | F | M4 | 1st relapse after ABMT | 80 | 74 | 89 | ND | Failure |
| 11 | 39 | M | M1 | 1st relapse under chemo | 44 | 38 | 64 | 70 | Failure |

The results showed 2 complete responses OCR), that being a response rate of 20%. Among the failures, 2 patients (no. 3 and no 7) showed a significant decrease of the percentage of medullary blasts, suggesting a certain effectiveness of IL2.

Various modifications of the method of the invention may be made without departing from the spirit or scope thereof and it should be understood that the invention is intended to be limited only as defined in the appended claims.

What is claimed is:

1. A method of treating chronic myeloid leukemia and acute myeloid leukemia in humans suffering from said leukemia and having more than 10% blast cells in the bone marrow consisting of administering to said humans intravenously by slow bolus or by continuous perfusion muscularly or subcutaneously at a dose of 2 to $20 \times 10^6$ U/M$^2$ per injection of human interleukin 2 (IL2) as the sole therapeutic agent.

2. The method of claim 1 wherein the leukemia is an acute myeloid leukemia.

3. The method of claim 1 wherein the IL2 is recombinant IL2 having a specific activity at least equal to $0.5 \times 10^7$ U BRMP/M$^2$.

4. The method of claim 3 wherein the $IL_2$ is non-glycoslated recombinant IL2 in reduced form.

5. The method of claim 3 wherein the IL2 is administered intravenously with slow bolus at a dose of about $8 \times 10^6$ U/M$^2$ per injection.

6. The method of claim 6 wherein the administration is effected two or three times per day over a cycle of five consecutive days per week.

7. The method of claim 6 wherein the administration of IL2 is effected in weeks 1, 3 and 5.

\* \* \* \* \*